United States Patent [19]

Gay

[11] 4,057,590

[45] Nov. 8, 1977

[54] PROCESS FOR MAKING PENTACHLORONITROBENZENE

[75] Inventor: Walter A. Gay, Cheshire, Conn.

[73] Assignee: Olin Corporation, New Haven, Conn.

[21] Appl. No.: 761,565

[22] Filed: Jan. 24, 1977

[51] Int. Cl.² .............................................. C07C 79/12
[52] U.S. Cl. ................................................. 260/646
[58] Field of Search ....................................... 260/646

[56] References Cited

U.S. PATENT DOCUMENTS

| | | | |
|---|---|---|---|
| 3,026,358 | 3/1962 | Lojewski | 260/646 |
| 3,984,487 | 10/1976 | Watts et al. | 260/646 |
| 4,026,955 | 5/1977 | Breaux et al. | 260/646 |

FOREIGN PATENT DOCUMENTS

| | | | |
|---|---|---|---|
| 620,338 | 5/1961 | Canada | 260/646 |

OTHER PUBLICATIONS

Jackson et al., J. Org. Chem., vol. 36, pp. 3638 to 3639.

*Primary Examiner*—Leland A. Sabastian
*Attorney, Agent, or Firm*—William A. Simons; Thomas P. O'Day; F. A. Iskander

[57] ABSTRACT

Process for making highly pure pentachloronitrobenzene (PCNB) by the nitration of pentachlorobenzene (PENTA).

13 Claims, No Drawings

PROCESS FOR MAKING PENTACHLORONITROBENZENE

BACKGROUND OF THE INVENTION

I. Field of Invention

This invention relates to a process for making pentachloronitrobenzene by the nitration of pentachlorobenzene. In particular, this invention relates to a process whereby highly pure pentachloronitrobenzene is produced. And, especially, this invention relates to a process for making pentachloronitrobenzene wherein the resultant levels of pentachlorobenzene and hexachlorobenzene impurities are extremely low.

II. Description of the Prior Art

Pentachloronitrobenzene (sometimes referred to herein as PCNB) is widely used today as a soil fungicide for many farming applications. While this use has shown many beneficial results, the present commercial products of PCNB have been questioned on environmental grounds because of the presence of two contaminants contained therein. These chemicals, pentachlorobenzene (sometimes referred to herein as PENTA) and hexachlorobenzene (sometimes referred to herein as HCB), have been found to bioaccumulate in the fatty tissue of animals. Therefore, their presence in this desirable soil fungicide, even in relative minor amounts, could cause a health hazard. For example, foodstuffs produced from soil which has been treated with quantities of impure fungicide may have PENTA and HCB leached into them and, thus, these impurities may accumulate in humans when they are eaten. Also, cattle and other livestock that graze on treated grass or ther pastures or grains may accumulate undesirable amounts of these impurities. And, furthermore, the farmer when applying PCNB to the soil may breathe in significant quantities of these impurities.

PCNB produced by prior art commercial processes usually contains at least about 0.5 to 2.0% or greater by weight each of PENTA and HCB. Although these percentages may appear to be minor amounts, they are still high enough to raise an increasingly stronger environmental concern by the manufacturers, consumers and the governmental regulatory agencies. In fact, a commercial PCNB product with less than about 0.2% by weight of either of these contaminants appears likely to be necessary in the future. However, since PENTA and HCB cannot be easily or economically separated from PCNB on large-scale commercial levels, an urgent need exists to develop a process for making PCNB in which the levels of these two other chemicals are minimized below what has previously been reached, preferably below 0.2% by weight level which may be required in the future.

In particular, commercial prior art processes for making PCNB have either chlorinated a chloronitrobenzene (see U.S. Pat. No. 3,026,358, issued on Mar. 20, 1962 to E. A. Lojewski) or have nitrated pentachlorobenzene with substantially pure nitric acid or a mixture of nitric and sulfuric acids. However, all of these processes have suffered from the high impurity problem cited above.

BRIEF SUMMARY OF THE INVENTION

The present invention, therefore, provides an improved process for making PCNB by which the levels of both PENTA and HCB impurities in the resulting product are each below about 0.5%, more preferably below 0.2%, by weight of the product. Specifically, the present process comprises reacting pentachlorobenzene with substantially pure nitric acid at a temperature from about 40° to about 85° C with the provisos that:

1. a weight ratio of said nitric acid to said pentachlorobenzene of at least about 3.0:1 is employed when the reaction is effected at a temperature in the range of about 40° to about 49° C;
2. a weight ratio of said nitric acid to said pentachlorobenzene of at least about 2.5:1 is employed when the reaction is effected at a temperature in the range of about 50° to about 59° C;
3. a weight ratio of said nitric acid to said pentachlorobenzene of at least about 2.0:1 is employed when the reaction is effected at a temperature in the range of about 60° to about 75° C; and
4. a weight ratio of said nitric acid to said pentachlorobenzene in the range of about 2.0:1 to about 3.5:1 is employed when the reaction is effected at a temperature in the range of about 76° to about 85° C.

DETAILED DESCRIPTION

The process of the present invention produces very pure PCNB because of the employment of a combination of three reaction parameters in the nitration of pentachlorobenzene. These parameters include the employment of (1) substantially pure nitric acid, (2) a reaction temperature range of from about 40° to about 85° C and (3) critical weight ratios of the nitric acid to pentachlorobenzene that vary with the reaction temperature. It has been found, in accordance with the present invention, that only by using all three of these parameters can an acceptable PCNB product be formed which contains less than 0.5% by weight each of the PENTA and HCB impurities.

The substantially pure nitric acid is employed in the present specification and claims attached thereto is defined to be (a) at least about 95% by weight pure $HNO_3$ and (b) containing no more than about 3% by weight water. For example, the substantially pure nitric acid may be 95% or higher $HNO_3$, 5% or less $H_2SO_4$ and the balance, i.e., always less than 3%, water. Other impurities which do not interfere with the reaction or significantly effect an increase in the amounts of PENTA and HCB in the product may also be present in the nitric acid in small amounts. This highly pure reactant is necessary because substantial impurities normally contained in commercial grades of nitric acids (i.e., sulfuric acid and water) can act as diluents and prevent the reaction from being substantially completed. This results in having an unacceptable amount of the PENTA reactant being left in the reaction mixture and thus contaminating the product. Preferably, the nitric acid is at least about 98%, most preferably at least about 99%, by weight pure $HNO_3$.

The pentachlorobenzene used herein can be obtained from any commercially available source. Most preferably, substantially pure (i.e., at least about 99% by weight) sources are desired so that purity of the resulting PCNB will not be lowered. However, unlike the nitric acid, substantially pure sources of PENTA are not necessary because the presence of impurities (e.g., usually tetrachlorobenzenes) therein normally will not affect the levels of PENTA and HCB in the desired product. Moreover, the pentachlorobenzene can be either in a molten state (at a temperature in the range of about 86° to about 150° C) or a solid powder. The solid state is preferred for its handling advantages, but the use of molten PENTA may be desirable for some applications.

According to the process of the invention, the reaction of pentachlorobenzene and nitric acid is carried out at a temperature range from about 40° to about 85° C, preferably from about 60° to about 75° C, and most preferably at about 62°-68° C. At temperatures below about 40° C, it has been found that the reaction proceeds too slowly so that appreciable amounts (i.e., over 0.5% by weight) of PENTA are left unreacted unless a prolonged reaction time (e.g., 24 hours) is employed. Above 85° C, it has also been found that the nitric acid starts to decompose. This decomposition is believed to cause the concentration of PENTA and HCB impurities in the product to rise. While the reason for this result is not clear, it is theorized that at these higher temperatures some of the nitric acid decomposes into water and nitrous oxides. The water so produced may act as a diluent to the reactant, causing the PENTA not to react more slowly. Furthermore, this decomposition may initiate side reactions which result in the production of HCB. At the preferred range of from about 60° to about 75° C, and, especially, at about 62°-68° C, the reaction speed is commercially viable and the production of these two impurities is minimized.

The third critical parameter of the present invention is the weight ratio of the nitric acid to pentachlorobenzene and its inter-relationship with the reaction temperature. This weight ratio should be at least about 3.0:1, preferably at least about 3.5:1, when the reaction is effected at a temperature in the range of about 40° to about 49° C. Further, this weight ratio should be at least about 2.5:1, preferably at least about 3.0:1, when the reaction is effected at a temperature in the range of about 50° C to about 59° C. And, when the reaction is carried out at the preferred temperature range of about 60° C to about 75° C, this weight ratio should be at least about 2.0:1, more preferably at least about 2.75:1 and most preferably in the range of about 3.0:1 to about 4.0:1. Finally, this weight ratio should be within the range of about 2.0:1 to about 3.5:1, preferably about 2.5:1 to about 3.25:1, when the reaction is effected at a temperature in the range of about 76° to about 85° C. While there is no maximum limit to the ratios of nitric acid to PENTA which are given above, as a practical matter weight ratios in excess of about 10:1, and preferably about 5:1, are generally undesirable for economic reasons.

Any suitable technique may be used in combining the nitric acid with the PENTA to effect the reaction. Usually, the present reaction is carried out by simply adding the PENTA to a reactor containing the substantially pure nitric acid. In that case, the addition rate should be slow enough so that the resulting exothermic reaction remains under control and the reaction temperature does not vary outside of the 40°-85° C limits. Furthermore, the present process may be carried out at any suitable pressure. Atmospheric pressures are not preferred because of the economic advantages inherent therein by not needing special equipment required for pressurized reactions. However, pressures above atmospheric can be employed when desired. Pressures below atmospheric normally are usually not desired because the nitric acid tends to vaporize therein, however, such reaction pressures are not excluded from the present invention.

The present reaction can be carried out with any conventional chemical reactor. This includes reactors that have glass or stainless steel linings. Preferably, the reactor is also equipped with an agitator for more uniform reaction. Agitation speeds have been found not to effect the product purity but relative slow speeds may produce larger crystals and relative fast speeds will produce smaller crystals of the product. Furthermore, the process can be carried out either on a continuous or batch basis.

In a preferred embodiment of the present invention, pentachlorobenzene is added to and reacted with at least 99% pure nitric acid wherein the reaction temperature is in the range from about 60° to about 75° C, most preferably from about 62° to about 68° C, and the weight ratio of the nitric acid to the pentachlorobenzene is at least 2.75:1, most preferably from about 3.0:1 to about 4.0:1. Normally, the addition rate of solid PENTA takes at least ½ hour, preferably from about 1 to 2 hours, for batch processes in order to control the exothermic reaction. If molten PENTA is employed, the addition rate should be even slower (i.e., dripping the PENTA very slowly into the reactor) so that the reaction temperature is not increased significantly. If has been found that the reaction is practically instantaneous upon addition. In some cases, it is desirable that some post addition mixing occur so as to ensure that all the PENTA will react with all the nitric acid. Normally, post reaction periods from about 15 minutes to five hours can be employed. This preferred embodiment of the present invention generally results in a product which contains less than 0.2% by weight each of PENTA and HCB impurities and most probably will meet or exceed environmental standards that may be set in the future.

After the reaction is completed (i.e., with or without the post addition mixing), the solid PCNB product will form in the reaction mixture which also contains spent nitric acid. Product recovery can then be achieved by any suitable technique or the PCNB may be employed with the reaction medium for further chemical reactions. Suitable recovery methods include any conventional liquid-solid separation means such as filtration, centrifuging, decanting and the like. Preferably, the PCNB product is recovered by filtering; followed by washing with a suitable solvent such as water to remove residuals from the reaction mixture. The spent nitric acid of the reaction medium can be either recycled or re-used for future reactions, preferably after treatment to ensure its purity.

The following examples and comparisons further illustrate the present invention. All parts and percentages are by weight unless otherwise expressly indicated.

EXAMPLE I

Into a three-neck 300 ml flask equipped with a mechanical agitator, thermometer and condensor was charged 150 g 99% by weight pure nitric acid (1% $H_2O$ impurity). The nitric acid was heated to 60°-65° C and, over a period of two hours, 50 g of 99.7% pure powdered pentachlorobenzene was added while the reaction mixture was stirred and the temperature maintained by slight air cooling at 60°-65° C. Following the addition, the reaction mixture was maintained at 60°-65° C for an additional four hours and then allowed to cool to about 30°-40° C (gas fuming is less at lower temperatures) at which point it is filtered by suction. The pentachloronitrobenzene product was pressed dry and washed twice with 100 mls water each time. After suitable drying with heat or at reduced pressure, the product was weighed and analyzed by Vapor Phase Chromatography (VPC). In this specific example, the product weighed 55.5 g (95% yeild); VPC analysis showed that the product was of exceptional quality with an assay of 99.77% pentachloronitrobenzene, 0.10% pentachlorobenzene and 0.04% hexachlorobenzene.

EXAMPLE II

The experiment in Example I was repeated by using at temperature of 70°–75° C. The product assay was 99.65% pentachloronitrobenzene, 0.06% pentachlorobenzene and 0.09% hexachlorobenzene.

EXAMPLE III

The experiment in Example I was repeated but with no post reaction period. The product assay was 99.60% pentachloronitrobenzene, 0.12% pentachlorobenzene and 0.05% hexachlorobenzene. This illustrates that no post reaction time is necessary, but that a slight decrease in pentachloronitrobenzene content may result if it is not used.

EXAMPLE IV

The experiment in Example I was repeated but using a post reaction time of 5 hours. The product assay was 99.73% pentachloronitrobenzene, 0.08% pentachlorobenzene and 0.05% hexachlorobenzene. This illustrates that maintaining the reaction mixture in a post reaction step for long periods of time is not detrimental to product quality.

EXAMPLE V

The experiment in Example I was repeated but using an addition time of one hour. The product assay was 99.80% pentachloronitrobenzene, 0.11% pentachlorobenzene and 0.03% hexachlorobenzene. This illustrates that the exothermic reaction can be sufficiently controlled without being detrimental to the product quality at twice the rate of addition.

EXAMPLE VI

The experiment in Example I was repeated but molten pentachlorobenzene is added drop-wise into the nitric acid over a 2-hour period. The temperature of the molten pentachlorobenzene was best maintained at 86°–150° C since below 86° C crystallization may occur with plugging of the addition line and since higher than 150° C may lead to partial sublimation. But this very slow addition of the molten PENTA did not change the reaction temperature. The product assay was 99.68% pentachloronitrobenzene, 0.08% pentachlorobenzene and 0.03% hexachlorobenzene. This illustrates the similarity of high quality product regardless of the physical state of the pentachlorobenzene.

EXAMPLE VII

The experiment in Example I was repeated with molten pentachlorobenzene and a 1-hour addition time. Product assay was 99.77% pentachloronitrobenzene, 0.06% pentachlorobenzene and 0.02% hexachlorobenzene. This illustrates the similarity of product quality using either solid or molten pentachlorobenzene under an additional set of conditions. This is to be compared to Example V.

EXAMPLE VIII

The experiment in Example I was repeated with molten pentachlorobenzene and no post reaction time. The product assay was 99.67% pentachloronitrobenzene, 0.09% pentachlorobenzene and 0.02% hexachlorobenzene. This illustrates the similarity of product quaility using solid or molten pentachlorobenzene under an additional set of conditions. This is to be compared to Example III.

EXAMPLE IX

The experiment in Example I was repeated except that 250 g molten pentachlorobenzene was added to 750 g 99% nitric acid. The product assay was 99.84% pentachloronitrobenzene, 0.07% pentachlorobenzene and 0.05% hexachlorobenzene. This illustrates that scale-up does not affect product purity.

EXAMPLE X–XVI

The experiment in Example I was repeated except for the changes indicated below in Table I. The time of the addition of the PENTA into the nitric acid was approximately about two hours for all of these examples.

TABLE I

| Ex. | Reaction Temperature (° C) | Wt. Ratio HNO$_3$:PENTA | Final Product Analysis %HCB | %PENTA |
|---|---|---|---|---|
| X | 40–45 | 3.0:1 | 0.01 | 0.24 |
| XI | 50–55 | 3.0:1 | 0.02 | 0.30 |
| XII | 60–65 | 2.0:1 | 0.03 | 0.38 |
| XIII | 60–65 | 2.5:1 | 0.04 | 0.35 |
| XIV | 70–75 | 2.0:1 | 0.09 | 0.50 |
| XV | 80–85 | 2.0:1 | 0.22 | 0.10 |
| XVI | 80–85 | 3.0:1 | 0.34 | 0.26 |

EXAMPLE XVII

The experiment in Example VI was repeated, but using 150 g of about 97% by weight pure nitric acid (also containing about 3% H$_2$O). The VPC product assay showed 0.02% hexachlorobenzene and 0.50% pentachlorobenzene.

EXAMPLE XVIII

The experiment in Example VI was repeated except for using 150 g of about 97% by weight pure nitric acid (also containing about 2% H$_2$SO$_4$ and about 1% by weight H$_2$O). The VPC product assay showed 0.04% hexachlorobenzene and 0.17% pentachlorobenzene.

EXAMPLE XIX

The experiment in Example VI was repeated except for using about 95% by weight pure nitric acid (also containing about 4% H$_2$SO$_4$ and about 1% H$_2$O). The VPC product assay showed 0.09% hexachlorobenzene and 0.15% pentachlorobenzene. Comparison of the results of Example VI with XVII–XIX shows that increasing the amount of H$_2$O in the nitric acid substantially raises the amount of PENTA impurity in the product, while increasing the amount of H$_2$SO$_4$ in the nitric acid (up to about 5%) only very slightly increases the amount of HCB impurity in the product.

EXAMPLE XX

The experiment of Example I was repeated except the reaction temperature was about 70°–75° C, the weight ratio of the nitric acid to the pentachlorobenzene was 2:1 and the nitric acid was 95% by weight pure (containing about 5% by weight H$_2$SO$_4$). The VPC product assay showed 0.05% HCB impurity and 0.43% PENTA impurity in the product.

EXAMPLE XXI

The experiment of Example I was repeated except the nitric acid was changed. These changes and the resulting VPC product analysis is shown in Table III below.

TABLE III

| Comparison | Reaction Temperature (° C) | Wt. Ratio HNO₃:PENTA | Purity of HNO₃ | | | Final Product Analysis | |
|---|---|---|---|---|---|---|---|
| | | | %HNO₃ | %H₂SO₄ | %H₂O | %HCB | %PENTA |
| XII | 60–65 | 3.0:1 | 93 | 0 | 7 | 0.11 | 3.80 |
| XIII | 60–65 | 3.0:1 | 95 | 0 | 5 | 0.03 | 1.60 |
| XIV | 60–65 | 3.0:1 | 93 | 6 | 1 | 0.40 | 1.70 | reaction temperature was about 70°–75° C and the nitric acid was 95% by weight pure (also containing about 5% H₂SO₄). The VPC product assay showed 0.13% HCB impurity and 0.41% PENTA impurity in the product.

EXAMPLE XXII

The experiment in Example I was repeated except a weight ratio of 2:1 of the nitric acid to pentachlorobenzene was used and the purity of the nitric acid was 95% by weight (also containing about 5% H₂SO₄). The VPC product assay showed 0.02% HCB impurity and 0.17% PENTA impurity.

COMPARISON I-VIII

The experiment of Example I was repeated except for the changes indicated in Table II below. The time of addition was approximately 2 hours.

TABLE II

| Comparison | Reaction Temperature (° C) | Wt. Ratio HNO₃:PENTA | Final Product Analysis | |
|---|---|---|---|---|
| | | | %HCB | %PENTA |
| I | 40–45 | 1.5:1 | 0.0 | 4.40 |
| II | 40–45 | 2.0:1 | 0.0 | 1.97 |
| III | 50–55 | 1.5:1 | 0.02 | 1.58 |
| IV | 50–55 | 2.0:1 | 0.0 | 0.60 |
| V | 60–65 | 1.5:1 | 0.04 | 0.84 |
| VI | 70–75 | 1.5:1 | 0.0 | 1.69 |
| VII | 80–85 | 1.5:1 | 0.21 | 2.74 |
| VIII | 80–85 | 4.0:1 | 0.71 | 0.29 |

COMPARISON IX

The experiment of Example I was repeated except that the reaction temperature was about 70°–75° C, the weight ratio of the nitric acid to the pentachlorobenzene was 2.0:1 and the purity of the nitric acid was 75% by weight (about 25% H₂SO₄ also contained therein). The VPC product analysis showed 0.10% HCB impurity and 1.12% PENTA impurity.

COMPARISON X

The experiment of the proceding comparison was repeated except that the weight ratio of the 75% nitric acid to the pentachlorobenzene was 3.0:1. Final VPC product anaylsis showned 0.23% HCB impurity and 1.13% PENTA impurity.

COMPARISON XI

The experiment of the preceding comparison was repeated except the reaction temperature was about 60°–65° C. Final VPC product analysis showed 0.07% HCB impurity and 22.9% PENTA impurity.

COMPARISONS XII–XIV

The experiment of Example VI using molten pentachlorobenzene reactant was repeated the purity of the

COMPARISON XV

Using the same equipment as in Example I, 50 g of pentachlorobenzene was added to 120 g of mixed acid (16.5% nitric acid and 83.5% sulfuric acid) in 2 hours at 65° C. After a post reaction time of 4 hours at 65° C, the reaction mixture was worked up and the product assay was found to be 58.27% pentachloronitrobenzene, 40.38% pentachlorobenzene and 0.29% hexachlorobenzene. This illustrates that the usual nitration reactant (mixed HNO₃/H₂SO₄) is detrimental to product purity under the conditions similar to those set forth in Example I.

What is claimed is:

1. The process for producing pentachloronitrobenzene comprising reacting pentachlorobenzene with substantially pure nitric acid at a temperature from about 40° to about 85° C, with the provisos that i. a weight ratio of said nitric acid to said pentachlorobenzene of at least about 3.0:1 is employed when the reaction is effected at a temperature in the range of about 40° to about 49° C;

ii. a weight ratio of said nitric acid to said pentachlorobenzene of at least about 2.5:1 is employed when the reaction is effected at a temperature in the range of about 50° to about 59° C;

iii. a weight ratio of said nitric acid to said pentachlorobenzene of at least about 2.0:1 is employed when the reaction is effected at a temperature in the range of about 60° to about 75° C; and iv. a weight ratio of said nitric acid to said pentachlorobenzene in the range of about 2.0:1 to 3.5:1 is employed when the reaction is effected at a temperature in the range of about 76° to about 85° C.

2. The process of claim 1 wherein said substantially pure nitric acid is at least about 99% by weight pure.

3. The process of claim 1 wherein said pentachlorobenzene is at least about 99% by weight pure.

4. The process of claim 1 wherein said reaction is carried out at a temperature in the range of about 62° to about 68° C and the weight ratio of said nitric acid to said pentachlorobenzene is in the range of about 3.0:1 to about 4.0:1.

5. The process of claim 1 wherein said weight ratio does not exceed about 10:1.

6. The process of claim 1 wherein said pentachlorobenzene is in a molten or solid state.

7. The process of claim 6 wherein said nitric acid is at least about 98% by weight pure.

8. The process of claim 7 wherein said reaction is carried out at a temperature in the range of about 60° to about 75° C and said weight ratio is at least about 2.75:1.

9. The process of claim 8 wherein said nitric acid is at least about 99% by weight pure.

10. The process of claim 9 wherein said weight ratio is in the range from about 3.0:1 to about 4.0:1.

11. The process of claim 10 wherein said reaction temperature is in the range of about 62° to about 68° C.

12. The process of claim 11 wherein said pentachlorobenzene is at least about 99% by weight pure.

13. The process of claim 12 wherein said pentachloronitrobenzene is recovered by filtration.

* * * * *

UNITED STATES PATENT OFFICE
CERTIFICATE OF CORRECTION

Patent No. 4,057,590                                Dated November 8, 1977

Inventor(s) Walter A. Gay

It is certified that error appears in the above-identified patent and that said Letters Patent are hereby corrected as shown below:

Column 1, line 33, "ther" should read --other--.

Column 2, line 36, "is" should read --as--.

Column 3, line 20, before the word "more" insert --or to react--.

Column 3, line 58, "not" should read --most--.

Column 4, line 22, "If" should read --It--.

Column 5, line 3, "yeild" should read --yield--.

Column 5, line 10, "at" should read --a--.

Column 7, line 54, "proceding" should read --preceding--.

Column 7, line 57, "showned" should read -showed--.

UNITED STATES PATENT OFFICE
CERTIFICATE OF CORRECTION

Patent No. 4,057,590  Dated November 8, 1977

Inventor(s) Walter A. Gay

It is certified that error appears in the above-identified patent and that said Letters Patent are hereby corrected as shown below:

Column 8, line 46, before "3.5:1" insert --about--.

Signed and Sealed this

Eighteenth Day of April 1978

[SEAL]

Attest:

RUTH C. MASON
Attesting Officer

LUTRELLE F. PARKER
Acting Commissioner of Patents and Trademarks